United States Patent [19]

Ng et al.

[11] Patent Number: 4,513,143

[45] Date of Patent: Apr. 23, 1985

[54] PREPARATION OF KETENE ACETALS

[75] Inventors: Steven Y. Ng, San Francisco; Donald W. Penhale, Cupertino; Jorge Heller, Woodside, all of Calif.

[73] Assignee: SRI International, Menlo Park, Calif.

[21] Appl. No.: 445,938

[22] Filed: Dec. 1, 1982

[51] Int. Cl.³ .................................... C07D 319/00
[52] U.S. Cl. .................................... 549/335; 568/596
[58] Field of Search ................ 549/335; 568/596

[56] References Cited

U.S. PATENT DOCUMENTS 3,829,504 8/1974 Hall et al. ............................ 549/453
4,304,767 12/1981 Heller et al. ........................ 424/78

OTHER PUBLICATIONS

Corey et al., J. Org. Chem. 38, 3224, (1973).

*Primary Examiner*—Ethel G. Love
*Attorney, Agent, or Firm*—Limbach, Limbach & Sutton

[57] ABSTRACT

Rearrangement of allyl acetals to ketene acetals is disclosed. The rearrangement is accomplished by mixing the allyl acetal with a solution of an alkali metal lower alkyl in a water-soluble primary amine. After several hours contact with the allyl acetal with the solution ketene acetal formed during the contact is separated from the reaction mixture.

8 Claims, No Drawings

PREPARATION OF KETENE ACETALS

DESCRIPTION

The invention described herein was made in the course of or under National Institutes of Health Contract No. 1-HD-7-2826 with the U.S. Department of Health, Education and Welfare.

TECHNICAL FIELD

This invention is directed to a method for rearranging allyl acetals and substituted allyl acetals produced ketene acetals.

BACKGROUND ART

U.S. Pat. No. 4,304,767 describes polymers of ketene acetals and polyols which are bioerodible and are suitable as carriers or matrices for therapeutic agents. These polymers containing entrapped therapeutic agents are bioerodible and when emplaced in a mammal they degrade and release the therapeutic agents entrapped in the polymer. The patent described methods for producing the precursor ketene acetals which are used in producing the bioerodible polymers. One of the methods for producing the ketene acetals which is described in the patent, involves the rearrangement of allyl acetals to produce the ketene acetals. The rearrangement methods proposed are characterized by low yields of the desired ketene acetal product and the ketene acetal product obtained in the rearrangement have a substantial content of impurities which are difficult to remove to a degree which produces a ketene acetal final product of sufficient purity to be useful in the production of the desired bioerodible polymers.

Pursuant to the method of the present invention, allyl acetals are rearranged to ketene acetals at high conversions and the ketene acetal product directly obtained by the method of the invention is readily purified to produce a polymer grade ketene acetal.

BRIEF DESCRIPTION OF THE INVENTION

Pursuant to the present invention, an allyl acetal or a substituted allyl acetal is added to a solution of an alkali metal lower mono-alkyl in water soluble primary amine. After standing for two to three hours at ambient or lower temperature the reaction mixture comes to a steady state in composition. The reaction mixture is then dispersed in cold water and the water mixture is extracted with a hydrocarbon solvent, such as pentane, to remove the organic materials from the water. The pentane phase is separated and dried and then the pentane is evaporated. The residue is redissolved in the hydrocarbon solvent and cooled to 10 to 20 centigrade degrees below zero to cause crystallization of the residue. The crystals are separated from the hydrocarbon by filtration and distilled under vacuum to obtain a highly purified ketene acetal product.

DETAILED DESCRIPTION OF THE INVENTION

The reaction pursuant to which allyl acetals are rearranged to ketene acetals are shown by the following illustrative equations:

For a monoallyl acetal:

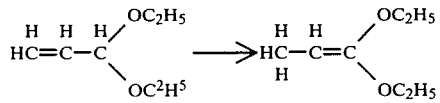

For a d-allylacetal:

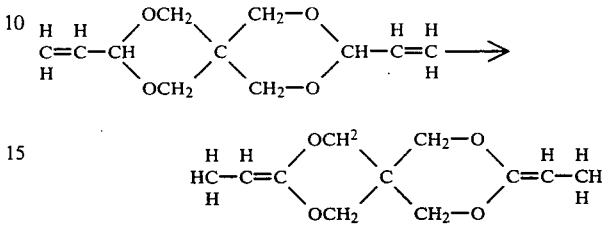

Conversion of diallyl acetals to diketene acetals is characterized by lower yields of the desired acetal product since in the case of the diallyl acetals the steady state composition of the reaction mixture obtained during rearrangement of the diacetals contains a proportion of material in which only one of the acetal groups has been rearranged to a ketene group and this material must be separated from the reaction mixture in order to obtain a pure diketene acetal product. The procedure for converting a diallyl acetal to a diketene acetal involves the following steps:

(a) dissolve a lower alkyl alkali metal compound in an amine solvent in a reaction vessel.

(b) maintain an inert atmosphere in the reaction vessel and add the allyl acetal reactant to the contents of the vessel. The amine component of the reaction mixture should be present in quantities sufficient to dissolve both the alkali metal alkyl and the allyl acetal. The molar proportions of alkyl alkali metal and allyl acetal should preferably be about 1 to 2 where the acetal is a monoallyl acetal and about 1 to 1 where the allyl acetal is a diallyl acetal.

(c) hold contents of the reaction vessel at a temperature in the range of about 10° to 40° C. for at least one-half hour to two to three hours. Higher temperatures up to about 100° C. or up to the boiling point of the amine component may be employed but no advantage accrues from the employment of higher temperatures.

(d) Pour the contents of the reaction vessel into ice water.

(e) Extract the mixture obtained in step (d) with a hydrocarbon solvent, such as pentane.

(f) Separate and dry a pentane extract layer from the mixture obtained in step (e). Evaporate the pentane.

(g) Dissolve the residue obtained in step (f) (the crude reaction product) in pentane. Preferably containing a small amount (about 0.1%) of triethylamine which acts as a stabilizer.

(h) Cool the pentane solution obtained in step (g) to temperatures about −10° to −20° C. to cause crystallization of the reaction product.

(i) Separate the crystals obtained in step (h) from the pentane by filtration.

(j) Subject the crystals obtained in step (i) to vacuum distillation to separate a minor content of non-volatile impurities and the distillate is taken as a final purified ketene product.

Practice of the process of the invention is described in the following examples.

EXAMPLE 1

7 liters of ethylene diamine were placed in a three-necked round bottom flask. The flask was cooled with ice and 7.8 mols of n-butyllithium dissolved in hexane were slowly added to the ethylene diamine. An argon atmosphere was maintained in the flask. 8.23 mols of diallylidine penta-erythritol were introduced into the flask and the resulting mixture was stirred for 3 hours while maintaining the flask temperature at 10° C. The reaction mixture was distributed in equal parts into six 4 liter beakers each containing 1.2 liters of ice water. 1.2 liters of pentane were stirred into the contents of each of the six beakers and then the contents were settled to separate an upper pentane extract phase in each beaker. The extract phases were separated, combined and washed with aqueous sodium carbonate. After washing the extract phases were dried with sodium carbonate—sodium sulfate and the pentane was evaporated.

The residue after evaporation weighed 1200 grams and by gas chromatographic analysis was found to contain 68.8% by weight of the diketene acetal 3,9-diethylidene-2,4,8,10 tetraoxyspiro undecane.

The 1200 gram product of the above reaction was combined with 518 grams of the product of a previous run. The 518 gram product had a diketene content of 91% by weight. The combined products were then purified as follows: The products were divided into 10 equal parts and each part was placed in a 2 liter flask. 1.4 liters of pentane containing 0.1% by weight of triethylamine were added to each flask. The flasks were then cooled to 0° C. and placed in a refrigerator. After 2 days standing the flasks were removed. Each of the flasks contained crystalline solid and a mother liquor. The mother liquors were decanted and then the crystalline material was removed from the flasks and crushed. The crushed crystals were then centrifuged under argon with dry ice cooling to −10° C. 1.2 kilograms of product were removed from the centrifuge and distilled under vacuum (0.1 mm) to remove a minor content of nonvolatile impurities.

Three distillation cuts were separated and put through gas chromatographic analysis. Cut characterizations were

| Cut # | Cut Wt. | Cut Purity % Diketene Product |
|---|---|---|
| 1 | 56 g | 98.0 |
| 2 | 478 g | 98.66 |
| 3 | 605 | 99.02 |

EXAMPLE 2

5.1 millimols of n-butyl lithium and 29.45 millimols of diallylidine pentaerythritol were dissolved in 50 millimeters of ethylenediamine in a 300 milliliter flask under an argon atmosphere. The progress of the run was followed by subjecting samples of the reaction product to gas chromatographic analysis as the run continued. The following table traces the progress of the run.

| Time | Temperature | Unreacted Feed | Half Reacted Feed | Fully Reacted Feed |
|---|---|---|---|---|
| 10 min. at | ambient | 69% | 29% | 5% |
| 1 hr. at | " | 50% | 38% | 11% |
| 2.5 hr. at | " | 48% | 37% | 11% |
| 1 hrs. at | 100° C. | 50% | 34% | 10% |

In the above table the times are indicated for times maintained at the temperature indicated. Unreacted feed means unreacted diallylidine pentaerythritol, half reacted feed means material in which one of the allylidine radicals has been converted to ketene and the other has not, and fully reacted feed means diketene product in which both of the allylidine groups has been rearranged to ketene.

In the above run the mol ratio of butyllithium to diallylidine pentaerythritol was low, i.e., 1 to 6, a ratio which is too low to produce high yields of the desired diketene product.

The holding of the reaction mixture at 100 degrees for one hour was to determine whether the application of higher temperature would change the composition of the reaction mixture which it did not do.

EXAMPLE 3

Two parallel runs following the procedure of Example 2 were made. In the first of the two runs the mol ratio of n-butyllithium to diallylidine Pentaerythritol was 1 to 2 and in the second of the runs the ratio of these two materials was 1 to 1.

The runs were followed by gas chromatographic analysis of the reaction material. The course of the runs and the product character are shown in the following table:

| | Temperature | Time | Unreacted Feed | Half Reacted Feed | Fully Reacted Feed |
|---|---|---|---|---|---|
| First Run | | | | | |
| n-butyllithium/feed ratio 1/2 | ambient | 1 hr. | 0% | 14.8% | 85.9% |
| | " | 4.5 hrs. | 0% | 7.2% | 92.8% |
| Second Run | | | | | |
| n-butyllithium/feed ratio 1/1 | ambient | 0.5 hr. | | 6.6% | 93.3% |
| | " | 5.0 hr. | | 5.6% | 94.3% |

From the table it is apparent that somewhat better conversions and yields were obtained when the higher mol ratio of butyllithium to feed was employed. The yield improvement is not great but it is significant in that the higher yields are usually attended by easier purification of the final product pursuant to the routine set forth in Example 1.

From consideration of the data presented in Examples 2 and 3 it is clear that the low mol ratio of butyllithium to allyl acetal produces unacceptably low conversions and yields. It further appears that acceptably high conversions and yields are obtained when the mol ratio of butyllithium to the allyl acetal is about 1 to 2. The allyl acetals employed in these examples are diallyl acetals and where a monoacetal is employed as the feed acceptable yields are obtained where the mol ratio of butyllithium to allyl acetal is 1 to 4. Putting this another way, it appears that for each allylic double bond contained in the acetal, one quarter mol of butyllithium should be employed in carrying out the rearrangement reaction.

EXAMPLE 4

Where substitubed allyl acetals are employed as the feed, it is more difficult to obtain high conversions and yields of desired ketene products than is the case with unsubstituted allyl acetals.

10 millimols of dimethallylidine pentaerythritol, 42 millimols of n-butyllithium and 60 milliliters of ethylene diamine were mixed in a reaction vessel. The vessel was heated to a temperature of 60° C. until solution was complete. The heating was then ceased and the solution was stirred at room temperature and the reaction was followed by gas chromatographic analysis. At the end of 3 hours a steady state composition had been reached in the reaction mixture and the crude reaction product consisted of 10% of the feed material, 45% of a half reacted product and 45% of a desired diketene. The reaction mixture was stirred for five days at room temperature and a further analysis was made but during the 5-day period there was no change in the ratio of the components of the crude reaction mixture.

EXAMPLE 5

15 ml of N-butylamine were placed in a three necked, 100 ml flask under argon. 20 millimols of n-butyl lithium were added and a light tan colored mixture formed. 11.78 millimols of diallylidine pentaerythritol were added to the flask contents and the resulting mixture was stirred at room temperature. After two hours an aliquat of the mixture was partitioned between water and pentane. The crude reaction product contained no unconverted feed and its major component was diketeneacetal.

EXAMPLE 6

Example 5 was repeated substituting di-propyl amine for n-butylamine. After two hours at room temperature the presence of ketene acetal in the reaction mixture could not be detected by gas chromatographic analysis. It appears that substitution of a secondary amine for a primary amine results in either no conversion or a very slow conversion of allyl acetal to ketene acetal.

In the foregoing examples the alkyl alkali metal employed is a lower alkyl lithium and the amines employed are ethylene diamine and normal butylamine.

Other alkyl alkali metal compounds are operable in the process of the invention but because of their higher reactivity their use requires very careful handling to avoid exposure to oxygen or water during the course of use. The alkyl groups of the metal alkyl may contain two to six carbon atoms.

Other primary amines than ethylene diamine and n-butylamine may also be employed but the amines must be water soluble to permit ready recovery of the ketene product from the reaction mixture and they should have boiling points above 40° C. to avoid the need to employ pressure reaction vessels to maintain them in liquid phase.

We claim:

1. A process for rearranging allyl acetals to produce ketene acetals which comprises intimately mixing an allyl acetal with an alkali metal lower alkyl dissolved in a water soluble primary amine and recovering a ketene acetal from the resultant mixture.

2. A process according to claim 1 wherein the alkali metal lower alkyl is n-butyllithium and the amine is ethylene diamine.

3. A process according to claim 2 wherein the allyl acetal is a mono allyl acetal and the molar ratio of metal alkyl to allyl acetal is in the range about 1:4 to 2:1.

4. A process according to claim 2 wherein the allyl acetal is a diacetal and the molar ratio of metal alkyl to acetal is in the range 1:2 to 4:1.

5. A process according to claim 1 wherein the process is carried out at ambient or lower temperatures.

6. A process according to claim 2 wherein the process is carried out at ambient or lower temperatures.

7. Process according to claim 4 wherein the diacetal is dimethallylidine pentaerythritol.

8. A process for converting a diallylacetal to a diketene acetal which comprises:
   a. dissolving an alkali metal lower alkyl in a water soluble primary amine in a reaction vessel, A
   b. maintaining an inert atmosphere in said reaction vessel and adding a diallylacetal to the contents of the reaction vessel in amount such that the mol ratio of alkali metal alkyl to diallylacetal is at least about 1 to 1;
   c. holding the contents of the reaction vessel in contact at a temperature at least about 10° C. for at least ½ hour;
   d. mixing the contents of the reaction vessel with cold water, adding a hydrocarbon solvent to the resulting aqueous mixture;
   e. agitating the mixture produced in step (d) and then settling the mixture to separate an upper hydrocarbon phase containing dissolved ketene product;
   f. evaporating the hydrocarbon solvent to leave a ketene residue product;
   g. dissolving the ketene residue product in a hydrocarbon solvent and cooling the solution to crystallize a purified diketene product.

* * * * *